US006727234B2

(12) United States Patent
Wiemer et al.

(10) Patent No.: US 6,727,234 B2
(45) Date of Patent: Apr. 27, 2004

(54) ISOPRENOID ANALOG COMPOUNDS AND METHODS OF MAKING AND USE THEREOF

(75) Inventors: David Wiemer, Iowa City, IA (US); Raymond J. Hohl, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 17 days.

(21) Appl. No.: 10/116,737

(22) Filed: Apr. 3, 2002

(65) Prior Publication Data

US 2003/0022869 A1 Jan. 30, 2003

Related U.S. Application Data

(60) Provisional application No. 60/281,170, filed on Apr. 3, 2001.

(51) Int. Cl.$^7$ .............................. A61K 31/66; C07F 9/40
(52) U.S. Cl. ......................... 514/129; 558/152; 558/155
(58) Field of Search ................................ 558/152, 155; 514/129

(56) References Cited

U.S. PATENT DOCUMENTS 5,574,025 A   11/1996 Anthony et al. ............ 514/129

OTHER PUBLICATIONS

Adjei, A.A., et al., "A Phase I Trial of the Farnesyl Transferase Inhibitor SCH66336: Evidence for Bioligical and Clinical Activity", *Cancer Research*, vol. 60, (Apr. 1, 2000), pp. 1871–1877.
Ashar, H.R., et al., "Farnesyl Transferase Inhibitors Block the Farnesylation of CENP-E and CENP-F and Alter the Association of CENP-E with the Microtubules", *The Journal of Biological Chemistry*, vol. 275, No. 39, (Sep. 29, 2000), pp. 30451–30457.
Bergo, M.O., et al., "Targeted Inactivation of the Isoprenylcysteine Carboxyl Methyltransferase Gene Causes Mislocalization of K–Ras in Mammalian Cells", *The Journal of Biological Chemistry*, vol. 275, No. 23, (2000), pp. 17605–17610.
Casey, P.J., et al., "Enzymatic modification of proteins with a geranylgeranyl isoprenoid", *Proc. Natl. Acad. Sci. USA*, vol. 88, (Oct., 1991), pp. 8631–8635.
Cermak, D.M., et al., "2–(Acyloxy)ethylphosphonate Analogues of Prenyl Pyrophosphates: Synthesis and Biological Characterization", *Bioorganic & Medicinal Chemistry*, vol. 8, (2000), 2729–2737.
Cermak, D.M., et al., "Synthesis of Nonracemic Dimethyl α–(Hydroxyfarnesyl)phosphonates via Oxidation of Dimethyl Farnesylphosphonate with (Camphorsulfonyl)oxaziridines", *J. Org. Chem.*, vol. 64, No. 2, (1999), pp. 388–393.
Chang, Jen–Wen, A., et al., "Stereoelectronic Effects on the Conformation and Kinetics of Nucleophilic Desplacement Reactions in Epimeric Six–membered Ring Phosphonate Diesters", *Tetrahedron*, vol. 43, No. 22, (1987), pp. 5187–5196.

Chehade, K.A., et al., "Design and Synthesis of a Transferable Farnesyl Pyrophosphate Analogue to Ras by Protein Farnesyltransferase", *J. Org. Chem.* vol. 65, No. 10, (2000), pp. 3027–3022.
Chen, Z., et al., "Both Farnesylated and Geranylgeranylated RhoB Inhibit Malignant Transformation and Suppress Human Tumor Growth in Nude Mice", *The Journal of Biological Chemistry*, vol. 275, No. 24, (Jun. 16, 2000), pp. 17974–17978.
Davisson, V.J., et al., "Phosphorylation of Isoprenoid Alcohois", *J. Org. Chem.* vol. 51, No. 25 (1986), pp. 4768–4779.
Ding, C.Z., et al., "Discovery and Structure–Activity Relationships of Imidazole–Containing Tetrahydrobenzodiazepine Inhibitors of Farnesyltransferase", *J. Med. Chem.*, vol. 42, No. 25, (1999), pp. 5241–5253.
Du, W., et al., "Geranylgeranylated RhoB Mediates Suppression of Human Tumor Cell Growth by Farnesyltransferase Inhibitors", *Cancer Research*, vol. 59, (Nov. 1, 1999), pp. 5492–5496.
Edamatsu, H., et al., "Cdk Inhibitors, roscovitine and olomoucine, synergize with farnesyltransferase inhibitor (FTI) to induce efficient apoptosis of human cancer cell lines", *Oncogene*, vol. 19, (2000), pp. 3059–3068.
Edelstein, R.L., et al., "Stereochemical Analysis of the Reaction Catalayzed by Yeast Protein Farnesyltransferase", *J. Org. Chem.*, vol. 63, No. 16 (1998), pp. 5298–5299.
Finder, J.D., et al., "Iinhibition of Protein Geranylgeranylation Causes a Superinduction of Nitric–oxide Synthase–2 by Interleukin–1β in Vascular Smooth Muscle Cells", *The Journal of Biological Chemistry*, vol. 272, No. 21, (May 23, 1997), pp. 13484–13488.
Flint, O.R., et al., "HMG CoA Reductase Inhibitor–Induced Myotoxicity: Pravastatin and Lovastatin Inhibit the Geranylgeranylation of Low–Molecular–Weight Proteins in Neonatal Rat Muscle Cell Culture", *Toxicology and Applied Pharmacology*, vol. 145, (1997), pp. 99–110.

(List continued on next page.)

Primary Examiner—Joseph K. McKane
Assistant Examiner—Kamal Saeed
(74) Attorney, Agent, or Firm—Schwegman, Lundberg, Woessner & Kluth, P.A.

(57) ABSTRACT

The invention provides compounds of formula I:

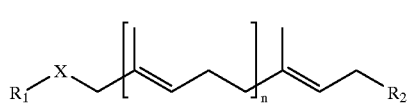

wherein X, $R_1$, $R_2$, and n have any of the values defined in the specification, and their pharmaceutically acceptable salts. The compounds are useful, for example, for blocking prenylation transferase enzymes, for probing or diagnosing protein prenylation processes, and for treating cancer in a mammal. The invention also provides pharmaceutical compositions, processes for preparing compounds of formula I, and intermediates useful for the synthesis of compounds of formula I.

28 Claims, 3 Drawing Sheets

OTHER PUBLICATIONS

Galbiati, F., et al., "The Dually Acylated NH$_2$–terminal Domain of G$_{i1}\alpha$ is Sufficient to Target a Green Fluorescent Protein Reporter to Caveolin–enriched Plasma Membrane Domains", *The Journal of Biological Chemistry*, vol. 274, No. 9, (Feb. 26, 1999), pp. 5843–5850.

Gaon, I., "Photoactive Analogs of Farnesyl Pyrophosphate Containing Benzoylbenzoate Esters: Synthesis and Application to Photoaffinity Labeling of Yeast Protein Farnesyltransferase", *J. Org. Chem.* vol. 61, No. 22 (1996), pp. 7738–7745.

Gibbs, R.A., et al., "A Pd(0)–Catalyzed Route to 13–Methylidenefarnesyl Diphosphate", *Tetrahedron Letters*, vol. 35, No. 16, (1994), pp. 2509–2512.

Gibbs, B.S., et al., "Novel Farnesol and Geranylgeranoil Analogues: A Potential New Class of Anticancer Agents Directed against Protein Prenylation", *J. Med. Chem.*, vol. 42, (1999), pp. 3800–3808.

Gorenstein, D.G., "Stereoelectronic Effects in Biomolecules", *Chem Rev.*, vol. 87, No. 5 (1987), pp. 1047–1077.

Hartwig, J.F., et al., "Synthesis and DNA–Binding Properties of a Cisplatin Analogue Containing a Tethered Dansyl Group", *J. Am. Chem. Soc.*, vol. 114, (1992), pp. 8292–8293.

Henry, K.J., et al., "Discovery of a Series of Cyclohexylethylamine–Containing Protein Farnesyltransferase Inhibitors Exhibiting Potent Cellular Activity", *J. Med. Chem.* vol. 42, No. 23, (1999), pp. 4844–4852.

Hohl, R.J., "Inhibition of Hydroxymethylglutaryl Coenzyme A Reductase Activity Induces a Paradoxical Increase in DNA Synthesis in Myeloid Leukemia Cells", *Blood*, vol. 77, No. 5, (Mar. 1, 1991), pp. 1064–1070.

Hohl, R.J., et al., "Stereochemistry–Dependent Inhibition of RAS Farnesylation by Farnesyl Phosphonic Acids", *Lipids*, vol. 33, No. 1, (1996), pp. 39–46.

Holstein, S.A., et al., "Phosphonate and Biphosphonate Analogues of Farnesyl Pyrophosphate as Potential Inhibitors of Farnesyl Protein Transferase", *Bioorganic & Medicinal Chemistry*, vol. 6, (1998), pp. 687–694.

Hunt, J.T., et al., "Discovery of (R)–7–Cyano–2,3,5,5–tetrahydro–1(1H–imidazol–4–ylmethyl)–3–(phenylmethyl)–4–(2–thienylsulfonyl)–1H–1, 4–benzodiazepine (BMS–214662), a Farnesyltransferase inhibitor with Potent Preclinical Antitumor Activity", *Journal of Medicinal Chemistry*, vol. 43, No. 20, (Oct. 5, 2000), pp. 3587–3595.

Jiang, K., et al., "The Phosphoinositide 3–OH Kinase/AkT2 Pathway as a Critical Target for Farnesyltransferase Inhibitor–Induced Apoptosis", *Molecular and Cellular Biology*, vol. 20, No. 1, (Jan., 2000), pp. 139–148.

Kang, M.S., et al. "Farnesyl–Derived Inhibitors of Ras Farnesyl Transferase", *Biochemical and Biophysical Research Communications*, vol. 217, No. 1, (1995), pp. 245–249.

Karp, J.E., et al., "Clinical and biologic activity of the farnesyltransferase inhibitor R115777 in adults with refractory and relapsed acute leukemias: a phase1 clinical–laboratory correlative trial", *Blood*, vol. 97, No. 11, (Jun. 1, 2001), pp. 3361–3369.

Liu, Ai–Xue, et al., "RhoB Alteration is Necessary for Apoptotic and Antineoplastic Responses to Farnesyltransferase Inhibitors", *Molecular and Cellular Biology*, vol. 20, No. 16, (Aug., 2000), pp. 6105–6113..

Long, S.B., et al., "Cocrystal Structure of Protein Farnesyltransferase Complexed with a Farnesyl Diphosphate Substrate", *Biochemistry*, vol. 37, No. 27, (1998), pp. 9612–9618.

Luckman, S.P., et al., "Nitrogen–containing Bisphosphonated Inhibit the Mevalonate Pathway and Prevent Post–Translational Prenylation of GTP–Binding Proteins, Including Ras", *Journal of Bone and Mineral Research*, vol. 13, No. 4, (1998), pp. 581–589.

McClard, R.W., et al., "Novel Phosphonylphosphinyl (P–C–P–C–) Analogues of Biochemically Interesting Diphosphates. Syntheses and Properties of P–C–P–C–Analogues of Isopentenyl Diphosphate and Dimethylallyl Diphosphate", *J. Am. Chem. Soc.*, vol. 109, (1987), pp. 5544–5545.

Mechelke, M.F., et al., "Preparation of (2E,6E)–10,11–Dihydrofarnesol via a (Bisphenyl)dithioacetal Reduction", *Tetrahedron Letters*, vol. 39, (1998), pp. 9609–9612.

Mechelke, M.F., et al., "Synthesis of Farnesol Analogues through Cu(i)–Mediated Displacements of Allylic THP Ethers by Grignard Reagents", *J. Org. Chem.*, vol. 64, No. 13, (1999), pp. 4821–4829.

Moasser, M.M., et al., "Farnesyl transferase inhibitors cause enhanced mitotic sensitivity to taxol and epothilones", *Proc. Natl. Acad. Sci. USA*, vol. 95, (Feb., 1998), pp. 1369–1374.

Mu, Y., "Cuprate–Mediated Synthesis and Biological Evaluation of Cyclopropyl– and tert–Buty(farnesyl Diphosphate Analogs", *J. Org. Chem.*, vol. 61, No. 23, (1996), pp. 8010–8015.

Mu, Y., et al., "On the Stereochemical Course of Human Protein–Farnesyl Transferase", *Jouran of the American Chemical Society*, vol. 117, No. 8, (Feb. 28, 1996), pp. 1817–1823.

Owen, D.J., et al., "Chemo–Enzymatic Synthesis of Fluorescent Rab 7 Proteins: Tools to Study Vesicular Trafficking in Cells", *Angew. Chem. Int. Ed.* vol. 38, No. 4, (1999), pp. 509–512.

Patel, D.V., et al., "Farnesyl Diphosphate–Based Inhibitors of Ras Farnesyl Protein Transferase", *J. Med. Chem.*, vol. 38, (1995), pp. 2908–2921.

Pompliano, D.L., et al., "Intramolecular Fluorescence Enhancement: A Continuous Assay of Ras Farnesyl: Protein Transferase", *J. Am. Chem. Soc.*, vol. 114, (1992), pp. 7945–7946.

Pompliano, D.L., "Steady–State Kinetic Mechanism of Ras Famesyl: Protein Transferase", *Biochemistry*, vol. 31, No. 15, (1992), pp. 3800–3807.

Roy, Marie–Odile, "Mutational and Biochemical Analysis of Plasma Membrane Targeting Mediated by the Farnesylated, Polybasic Carboxy Terminus of K–ras4B", *Biochemistry*, vol. 39, (2000), pp. 8298–8307.

Sepp–Lorenzino, L., et al., "A Peptidomimetic Inhibitor of Farnesyl:Protein Transferase Blocks the Anchorage–dependent and –independent Growth of Human Tumor Cell Lines", *Cancer Research*, vol. 55,(Nov. 15, 1995), pp. 5302–5309.

Sun, J., et al., "Antitumor Efficacy of a Novel Class of Non–thiol–containing Peptidomimetic Inhibitors of Farnesyltransferase and Geranylgeranyltransferase I: Combination Therapy with the Cytotoxic Agents Cisplatin, Taxol, and Gemcitabine", *Cancer Research*, vol. 59, (Oct. 1, 1999), pp. 4919–4928.

Tahir, S.K., et al., "Inhibition of farnesyltransferase with A–176120, a novel and potent farnesyl pyrophosphate analogue", *European Journal of Cancer*, vol. 36, (2000), pp. 1161–1170.

Thurmond, D.C., et al., "Regulation of Insulin–stimulated GLUT4 Translocation by Munc18c in 3T3L1 Adipocytes", *The Journal of Biological Chemistry*, vol. 273, No. 50, (1998), pp. 33876–33883.

Valentijn, A.R.P.M., et al., "Synthesis of Pyrophosphonic Acid Analogues of Farnesyl Pyrophosphate", *Tetrahedron*, vol. 51, No. 7, (1995), pp. 2099–2108.

Van Beek, E. et al., "Farnesyl Pyrophosphate Synthase is the Molecular Target of Nitrogen–Containing Bisphosphonates", *Biochemical and Biophysical Research Communications*, vol. 264, No. 1, (1999), pp. 108–111.

Yamamoto, Y., et al., "The Dansyl Group as a Molecular Probe for the Histochemical Localization of a Synthetic Fibronectin–related Peptide", *Chemistry Letters*, (1994), pp. 1379–1382.

Zahn, T.J., "Evaluation of Isoprenoid Conformation in Solution and in the Active Site of Protein–Farnesyl Transferase using Carbon–13 Labeling in Conjunction with Solution– and Solid–State NMR", *Journal of American Chemical Society*, vol. 122, No. 30, (Aug. 2, 2000), pp. 7153–7164.

Zahn, T.J., et al., "Synthesis and Conformational Analysis of Di–$^{13}$C–Labeled Farnesyl Diphosphate Analogs", *Tetrahedron Letters*, vol. 39, (1998), pp. 3991–3994.

Zujewski, J., et al., "Phase I and Pharmacokinetic Study of Farnesyl Protein Transferase Inhibitor R115777 in Advance Cancer", *Journal of Clinical Oncology*, vol. 18, No. 4, (Feb., 2000), pp. 927–941.

ISOPRENOID ANALOG COMPOUNDS AND METHODS OF MAKING AND USE THEREOF

CROSS-REFERENCE TO RELATED APPLICATIONS

This non-provisional U.S. Patent Application claims priority to U.S. Provisional Patent Application Serial No. 60/281,170, filed Apr. 3, 2001, entitled "FLUORESCENT PROBES OF PROTEIN PRENYLATION".

BACKGROUND OF THE INVENTION

Prenylation of proteins is a common form of post-translational processing found in many biological systems. For example, at least 300 human proteins are prenylated and many of these proteins play critical roles in essential signal transduction pathways. Mevalonic acid derivatives, known collectively as isoprenoids, are known to be central to mammalian metabolism, but the smaller intermediates in this pathway were viewed primarily as precursors to larger compounds such as steroids and dolichols. Not until 1989 was the presence of prenylated cysteines demonstrated in mammalian cells. The number of prenylated proteins continues to grow, with sequences for at least 300 prenylated proteins now recognized in humans corresponding to about 1% of the total cellular protein by mass. These include all of the known monomeric and trimeric G proteins, proteins which play central roles in a variety of signal transduction processes that regulate cell growth. Therefore, inhibition or modification of protein prenylation processes is a promising area for the development of new therapeutic agents and treatment methods, for example, anticancer agents and cancer treatments. Additionally, diagnosis or treatment regimes directed toward inhibition or modification of protein prenylation processes can be improved and refined with the help of enhanced means and methods of detecting changes in vivo or in vitro in the prenylation process.

Goody reported the preparation of detectable terpenoid analog compounds as substrates for GGPTase II in vitro. (*Angew. Chem., Int. Ed. Eng.*, 1999, 38, 509–512; See also J. Davisson, et al. *J. Org. Chem.* 1986, 51, 4768–4779.) However, potential biologic and chemical instability considerations of these compounds may limit their utility, for example, in in vivo experiments where intracellular esterases can cleave the anthranilic ester linkage to the component parts thereby liberating a fluorescent anthranilic acid.

Other publications of interest are listed in the references section below.

U.S. Pat. Nos. 5,998,204 and 6,197,928 are of general interest and relate to fluorescent protein sensors for detection of analytes, for example, localization sequences for prenylation or for insertion into a plasma membrane (CaaX) CAAX [(SEQ ID NO:51]).

Thus, there is a continuing need for compounds which can inhibit the prenylation process, and have improved stability, improved spectral detectability, or both.

SUMMARY OF THE INVENTION

The present invention provides analog compounds of key intermediates of isoprenoid biosynthesis and metabolism. These analogs can be prepared through chemical synthesis and can function as alternate substrates for enzymes involved in post-translation processing in either in vitro or in vivo. The compounds of the invention can be potent prenylation process inhibitor compounds which can also have improved stability, improved spectral detectability, or both. The compounds of the invention are also useful as probes for studying the prenylation process and related processes.

The invention provides a compound of formula I:

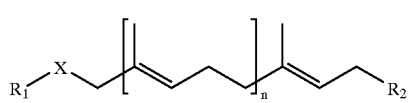

wherein:
X is independently —NR$_a$—, O, or S;
R$_1$ is a detectable group;
R$_2$ is independently
  OH,
  (C$_1$–C$_{10}$)alkanoyloxy,
  —O—P(=O)(—OR$_a$)$_2$,
  —O—P(=O)(—OR$_a$)—O—P(=O)(—OR$_a$)$_2$,
  —CH$_2$—O—P(=O)(—OR$_a$)$_2$,
  —CH$_2$—O—P(=O)(—OR$_a$)—O—P(=O)(—OR$_a$)$_2$,
  —CH$_2$—P(=O)(—OR$_a$)$_2$,
  —CH{—P(=O)(—OR$_a$)$_2$}$_2$,
  —CH$_2$—P(=O)(—OR$_a$)—O—P(=O)(—OR$_a$)$_2$,
  —CH=CH{—P(=O)(—OR$_a$)$_2$}, or
  —CH=C{—P(=O)(—OR$_a$)$_2$}$_2$;
each R$_a$ is independently hydrogen, (C$_1$–C$_{10}$)alkyl, (C$_1$–C$_{10}$)alkanoyl, (C$_1$–C$_{10}$)alkanoyloxy, (C$_1$–C$_{10}$)alkoxycarbonyl, or —CH$_2$—O—(C$_1$–C$_{10}$)alkanoyl;
n is independently 1, 2, or 3;
or a pharmaceutically acceptable salt thereof.

The invention also provides a pharmaceutical composition comprising a compound of formula I and a pharmaceutically acceptable diluent or carrier.

The invention also provides a method of treating cancer, comprising administering to a mammal afflicted with cancer, an amount of a compound of the invention effective to treat the cancer.

The invention also provides a method of inhibiting a prenylation transferase or synthase enzyme comprising contacting the enzyme in vivo or in vitro with an effective amount of a compound of the invention.

The invention also provides a method of accessing the metabolic status of an enzyme, such as a prenylation transferase enzyme, comprising:
  contacting the enzyme with an effective amount of a mixture of a farnesol analog compound of the invention and a geraniol or geranylgeraniol analog compound of the invention, and as described herein; and
  measuring the relative ratio, or levels, of farnesylation to geranylgeranylation of the farnesol and geraniol or geranylgeraniol analog compounds accomplished by the enzyme, and wherein the ratio correlates with the metabolic status of the enzyme.

The invention also provides a compound of the invention for use in medical therapy or diagnosis, for example, treating cancer.

The invention also provides for the use of a compound of the invention for the manufacture of a medicament useful for the treatment of cancer.

The invention also provides for the use of a compound of the invention for the manufacture of a medicament useful for inhibiting prenylation transferase or synthase enzymes in a mammal.

The invention also provides processes and intermediates disclosed herein that are useful for preparing compounds of the invention. Some compounds of the formula I are useful as intermediates in preparing other compounds of formula I.

DETAILED DESCRIPTION

Figure 1:
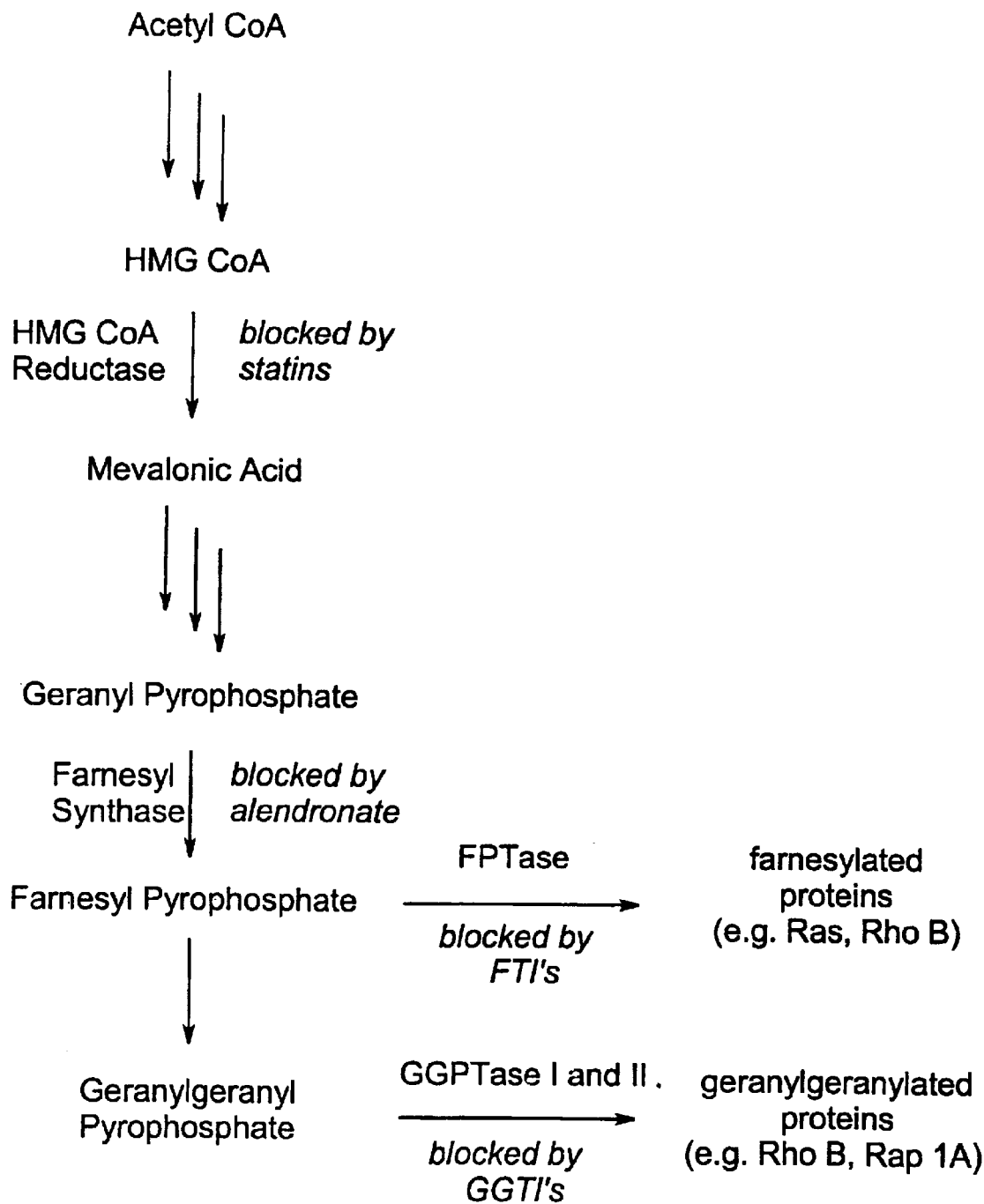
FIG. 1 schematically illustrates isoprenoid biosynthesis and protein prenylation routes in embodiments of the present invention.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Het" is a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring, or any cyclic heterocycle group which may be monocyclic or multi-cyclic. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a monovalent saturated or partially unsaturated cyclic non-aromatic group which contains at least one heteroatom, preferably 1 to 4 heteroatoms, selected from nitrogen ($NR_x$, wherein $R_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

The term "detectable group" refers to any known fluorophore substituent, for example, fluorescent groups including, but not limited to, anthranilic acid compounds, aminonaphthalenesulfonic acid compounds, coumarin compounds, and like groups or compounds and as illustrated herein.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "therapeutically effective amount" refers to that amount of a compound of the invention which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of formula I are where, for example, an exchangeable group, such as hydrogen in —OH, —NH—, or —P(=O)(OH)—, is replaced with a pharmaceutically acceptable cation (e.g. a sodium, potassium, or ammonium ion) and can be conveniently be prepared from a corresponding compound of formula I by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine transferase inhibitory activity using the standard tests described herein, or using other similar tests which are well known in the art. In particular, it is understood that compounds of formula I, such as $R_1$, $R_2$, or substituents thereon, can exist in the corresponding tautomeric "enol" form, and that such tautomers are included as compounds of the invention.

Specific and preferred values listed below for radicals, substituents and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_1-C_{10})$alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy or decyloxy; $(C_2-C_6)$alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_1-C_{10})$alkanoyl can be acetyl, propanoyl, butanoyl, pentanoyl, hexanoyl, heptanoyl, octanoyl, nonanoyl, or decanoyl; $(C_1-C_{10})$alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, octyloxycarbonyl, nonyloxycarbonyl or decyloxycarbonyl; $(C_1-C_{10})$alkanoyloxy can be formyloxy, acetoxy, propanoyloxy, butanoyloxy, isobutanoyloxy, pentanoyloxy, hexanoyloxy, heptanoyloxy, octanoyloxy, nonanoyloxy, or decanoyloxy; aryl can be phenyl, indenyl, naphthyl, or anthracenyl; heterocycle can benztriazolyl, triazinyl, oxazoyl, isoxazolyl, oxazolidinoyl, isoxazolidinoyl, thiazolyl, isothiazoyl, pyrazolyl, imidazolyl, pyrrolyl, pyrazinyl, pyridinyl, morpholinyl, quinolinyl, isoquinolinyl, indolyl, pyrimidinyl, piperidinyl, pyrrolidinyl, morpholinyl, thiomorpholinyl, or piperazinyl; and heteroaryl can be, for example, furyl, imidazolyl, triazolyl, triazinyl, oxazoyl, isoxazoyl, thiazolyl, isothiazoyl, pyrazolyl, pyrrolyl, pyrazinyl, tetrazolyl, 1-methyl-1H-tetrazol-5-yl, pyridyl, (or its N-oxide), thienyl, pyrimidinyl (or its N-oxide), indolyl, isoquinolyl (or its N-oxide) or quinolyl (or its N-oxide).

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_1-C_6)$alkoxy can be methoxy, ethoxy, propoxy, isopropoxy, butoxy, iso-butoxy, sec-butoxy, pentoxy, 3-pentoxy, or hexoxy.

A specific compound of formula I is the formula II:

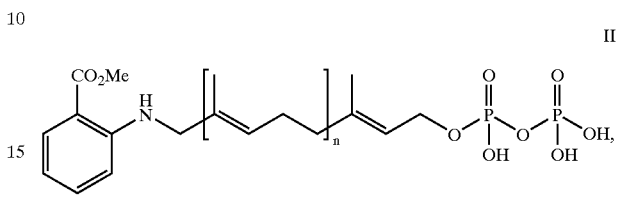

where $R_1$ is a 2-methoxycarboxy phenyl detectable group, $R_2$ is diphosphate ester, n=1 to 3, and X is NH; or a pharmaceutically acceptable salt thereof.

Another specific compound of formula I is the formula III:

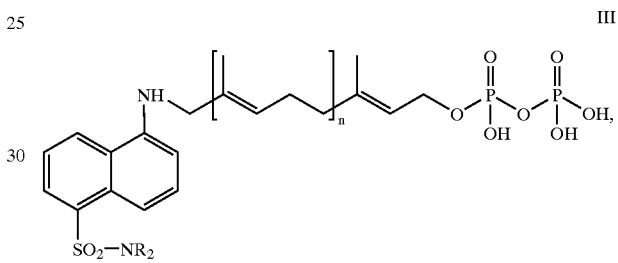

where n=0 to 3, and R is $(C_1-C_{10})$alkyl, for example, methyl; or a pharmaceutically acceptable salt thereof.

A specific value for $R_1$ is a detectable group, such as a known fluorophore substituent.

A specific value for $R_1$ is an aryl group, such as phenyl, naphthyl, or anthracenyl, which aryl group is optionally substituted with one or more substituents independently selected from —COOR$_b$, —S(O)$_n$NR$_b$R$_b$, halo, cyano, nitro, aryl, heterocycle, $(C_2-C_6)$alkenyl, —C(=O)NR$_b$R$_b$, —OC(=O)NR$_b$R$_b$, —NR$_b$R$_b$, or —S(O)$_n$R$_b$, where each R$_b$ is independently hydrogen, $(C_1-C_{10})$alkyl, or $(C_1-C_{10})$alkanoyl.

Another specific value for $R_1$ is Het, for example a heterocycle or heteroaryl, such as anthranil or quinoline, which Het is optionally substituted with one or more substituents independently selected from —COOR$_b$, —S(O)$_n$NR$_b$R$_b$, halo, cyano, nitro, aryl, heterocycle, $(C_2-C_6)$alkenyl, —C(=O)NR$_b$R$_b$, —OC(=O)NR$_b$R$_b$, —NR$_b$R$_b$, or —S(O)$_n$R$_b$, where each R$_b$ is independently hydrogen, $(C_1-C_{10})$alkyl, or $(C_1-C_{10})$alkanoyl.

Another specific value for $R_1$ is substituted phenyl.

Another specific value for $R_1$ is phenyl substituted with a —COOR$_b$.

Another specific value for $R_1$ is 2-methoxycarboxy phenyl.

Another specific value for $R_1$ is substituted naphthyl.

Another specific value for $R_1$ is naphthyl substituted with a —S(O)$_n$NR$_b$R$_b$.

Another specific value for $R_1$ is naphthyl substituted at the 5-position with a —S(O)$_n$NR$_b$R$_b$ substituent.

Another specific value for $R_1$ is 5-N,N'-dimethylaminosulfonyl naphthy-1-yl.

A specific value for $R_2$ is OH.

Another specific value for is $(C_1-C_{10})$alkanoyloxy.

Another specific value for $R_2$ is —O—P(=O)(—OR$_a$)$_2$.

Another specific value for $R_2$ is —O—P(=O)(—OR$_a$)—O—P(=O)(—OR$_a$)$_2$.

Another specific value for $R_2$ is —CH$_2$—O—P(=O)(—OR$_a$)$_2$.

Another specific value for $R_2$ is —CH$_2$—O—P(=O)(—OR$_a$)—O—P(=O)(—OR$_a$)$_2$.

Another specific value for $R_2$ is —CH$_2$—P(=O)(—OR$_a$)$_2$.

Another specific value for $R_2$ is —CH{—P(=O)(—OR$_a$)$_2$}$_2$.

Another specific value for $R_2$ is —CH$_2$—P(=O)(—OR$_a$)—O—P(=O)(—OR$_a$)$_2$.

Another specific value for $R_2$ is —CH=CH {—P(=O)(—OR$_a$)$_2$}.

Another specific value for $R_2$ is —CH=C{—P(=O)(—OR$_a$)$_2$}$_2$.

A specific value for $R_a$ is hydrogen.

A specific value for $R_a$ is —C(=O)—CH$_3$.

Another specific value for $R_a$ is —CH$_3$.

Another specific value for $R_a$ is —CH$_2$—O—$(C_1-C_6)$ alkanoyl.

A specific value for $R_b$ is hydrogen.

Another specific value for $R_b$ is —CH$_3$.

A specific value for n is 1.

Another specific value for n is 2.

Another specific value for n is 3.

A specific value for X is —NR$_a$—.

A specific value for X is —NH—.

A specific value for X is —N(CH$_3$)—.

A specific value for X is —O—.

A specific value for X is —S—.

A specific value for a protein conjugate of the present invention is a protein linked to a fluorescent fragment of a compound of the invention, for example, the Ras adduct of the compound of formula I, such as compounds of the formula II or III.

Processes and novel intermediates useful for preparing compounds of formula I are provided as further embodiments of the invention and are illustrated by the following procedures in which the meanings of the generic radicals are as given above unless otherwise qualified. Compounds of formula I and preceding intermediates wherein $R_1$, $R_2$, and n have any of the values, specific values, or preferred values defined herein, can be prepared in accordance with the preparative schemes described below.

The invention provides a pharmaceutical composition, comprising an effective amount of a compound of formula I as described hereinabove; or a pharmaceutically acceptable salt thereof; and a pharmaceutically acceptable carrier. The present compositions are preferably presented in a form suitable for absorption by the gastro-intestinal tract.

The compounds of formula I can be formulated as pharmaceutical compositions and administered to a mammalian host, such as a human patient in a variety of forms adapted to a selected route of administration, i.e., by oral, parenteral, intravenous, intramuscular, topical, or subcutaneous routes. Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

For veterinary medicine, the composition may, for example, be formulated as an intra-mammary preparation in either long acting or quick-release bases.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The compositions per unit dosage, whether liquid or solid may contain from 0.1% to 99% of active material (compound I or salts thereof), the preferred range being from about 10–60%. The composition will generally contain from about 15 mg to about 1,500 mg by weight of active ingredient based upon the total weight of the composition; however, in general, it is preferable to employ a dosage amount in the range of from about 250 mg to 1,000 mg. In parenteral administration the unit dosage is usually the pure compound in a slightly acidified sterile water solution or in the form of a soluble powder intended for solution. Single dosages for injection, infusion or ingestion may be administered, i.e., 1–3 times daily, to yield levels of about 0.5–50 mg/kg, for adults.

The ability of a compound of the invention to function as a transferase inhibitor or blocker can be demonstrated using the test methods described below, or using other tests which are well known in the art. Representative compounds of formula I can be readily evaluated as inhibitors the above mentioned transferases by, for example, relative $IC_{50}$ analysis.

The present invention provides chemical syntheses of fluorescent analogs of farnesol (FOH), farnesyl pyrophosphate (FPP), geranylgeraniol (GGOH), and geranylgeranyl pyrophosphate (GGPP). These analogs can be designed to display minimal differences from the natural substrates to maximize the possibility that they can be incorporated into various lipoproteins.

The present invention suggests in vitro testing of the compounds of the present invention with prenyl transferases and their protein substrates to demonstrate inhibition of modified proteins. For example, experiments with isolated Ras proteins, normal isoprenoid substrates, and farnesyl protein transferase should give unprenylated proteins.

The present invention suggests in vitro testing of the compounds of the present invention with prenyl transferases and their protein substrates to demonstrate formation of unnaturally modified proteins. For example, experiments with isolated Ras proteins and farnesyl protein transferase should give "farnesylated" proteins carrying fluorescent labels and provide protein standards for in vivo experiments.

The present invention suggests in vivo testing of the compounds of the present invention in cell lines to determine if the fluorescent isoprenoid analogs serve as inhibitors for the enzymes that convert proteins to prenylated lipoproteins, ultimately resulting in the accumulation of unmodified proteins and reduction in prenylated proteins in living cells. These experiments can be accomplished in normal culture media or with cells depleted of natural isoprenoids (e.g., by treatment with lovastatin).

The present invention suggests in vivo testing of the compounds of the present invention in cell lines to determine if the fluorescent isoprenoid analogs serve as substrates for the enzymes that convert proteins to prenylated lipoproteins, ultimately providing fluorescent prenylated proteins in living cells. These experiments can be done in normal culture media or with cells depleted of natural isoprenoids (e.g., by treatment with lovastatin).

The present invention provides chemical synthesis of analogs of the natural isoprenoids doubly modified to re-direct post-translational processing and label the resulting proteins with fluorescent tags.

The present invention provides a method for the analysis of cellular traffic in prenylated proteins, for example, using confocal microscopy to monitor localization of prenylated proteins carrying fluorescent labels. These experiments can be done initially under conditions as natural as possible and then in the presence of representative FPTase inhibitors or alternative substrates designed to redirect post-translational processing.

The following discussion, figures, and examples further describe and exemplify making and using the present invention.

Three prenylation motifs are known and each is recognized by a specific prenyl transferase. A first prenyl transferase is the enzyme farnesyl protein transferase (FTase or FPTase) recognizes a carboxyl terminal amino acid sequence described as a "—CAAX box," where C is cysteine, A is any aliphatic amino acid, and X is serine, methionine, glutamine, or alanine. FPTase transfers a farnesyl group from farnesyl pyrophosphate (FPP) to the sulfhydryl group of the cysteine. The resultant protein is further processed by proteolytic cleavage of the three C-terminal amino acids in a reaction catalyzed by the protease RCE1, and then methylation of the newly freed carboxyl group through reaction catalyzed by the enzyme Icmt. The net effect of these transformations is transformation of a hydrophilic protein found primarily in the cytosol to a hydrophobic protein found primarily in association with a lipid membrane.

A second prenyl transferase (GGTase or GGPTase I) is closely related to FPTase in its structure and substrate specificity. This enzyme transfers a geranylgeranyl group from geranylgeranyl pyrophosphate (GGPP) to a cysteine sulfhydryl group in proteins bearing a —CAAX box where the terminal amino acid is a leucine. It is highly selective for transfer of a geranylgeranyl group but also will bind FPP and catalyze transfer of a farnesyl group to some substrates.

A third enzyme known to transfer prenyl groups to proteins is geranylgeranyl transferase II (GGTase II or GGPTase II) also referred to as Rab geranylgeranyl transferase. Until very recently this enzyme was thought to have an absolute specificity for GGPP and not bind FPP, but this has now been questioned. Its protein substrates differ significantly from those of GGPTase I in that two cysteine residues are required at, or adjacent to, the carboxyl terminus in amino acid sequences such as -XXCC, -XCXC, or -CCXX. Finally, short peptides bearing these sequences are not substrates for this enzyme, while short sequences with the -CAAX box do serve as substrates for FPTase and/or GGPTase I.

Figure 2:
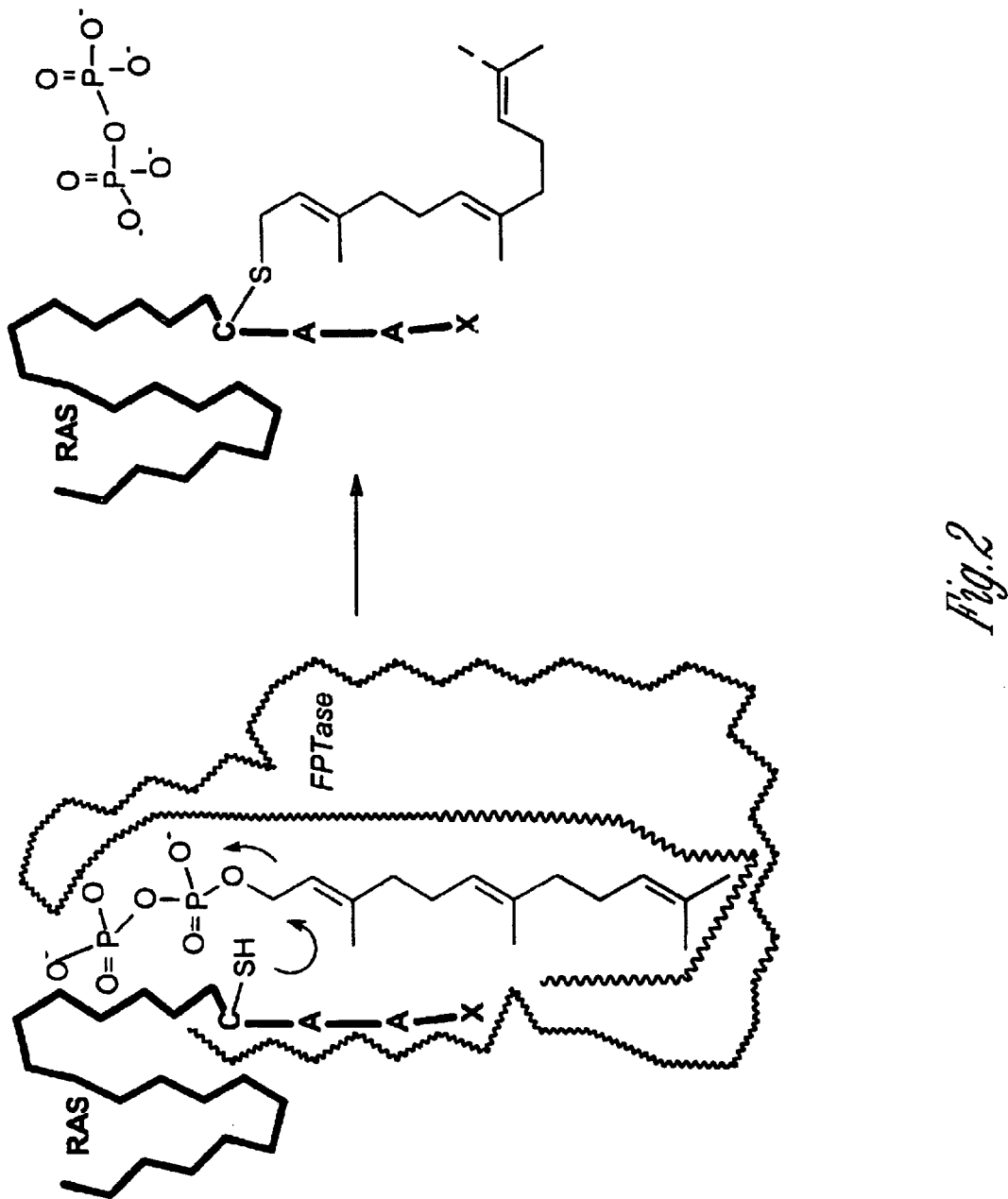
FIG. 2 schematically illustrates normal RAS farnesylation in embodiments of the present invention.

FIG. 2 shows schematically the overall mechanism of RAS farnesylation involves FPTase catalyzed nucleophilic attack of the —SH group of the cysteine in the -CAAX box on the C-1 position of farnesyl pyrophosphate. Whether by an $S_N^1$ or $S_N^2$ mechanism, or some intermediate variant possible only in the enzyme's active site, this results in displacement of pyrophosphate and formation of a new covalent bond between RAS and the farnesyl group. A inhibition strategy for interrupting this process is one using compound analogs where a phosphate group is not readily lost. For example, various farnesylphosphonates, wherein a carbon-phosphorus bond joins the phosphoryl group to the farnesyl chain, incorporate this essential property along with a highly desirable similarity to the natural substrate.

Figure 3:
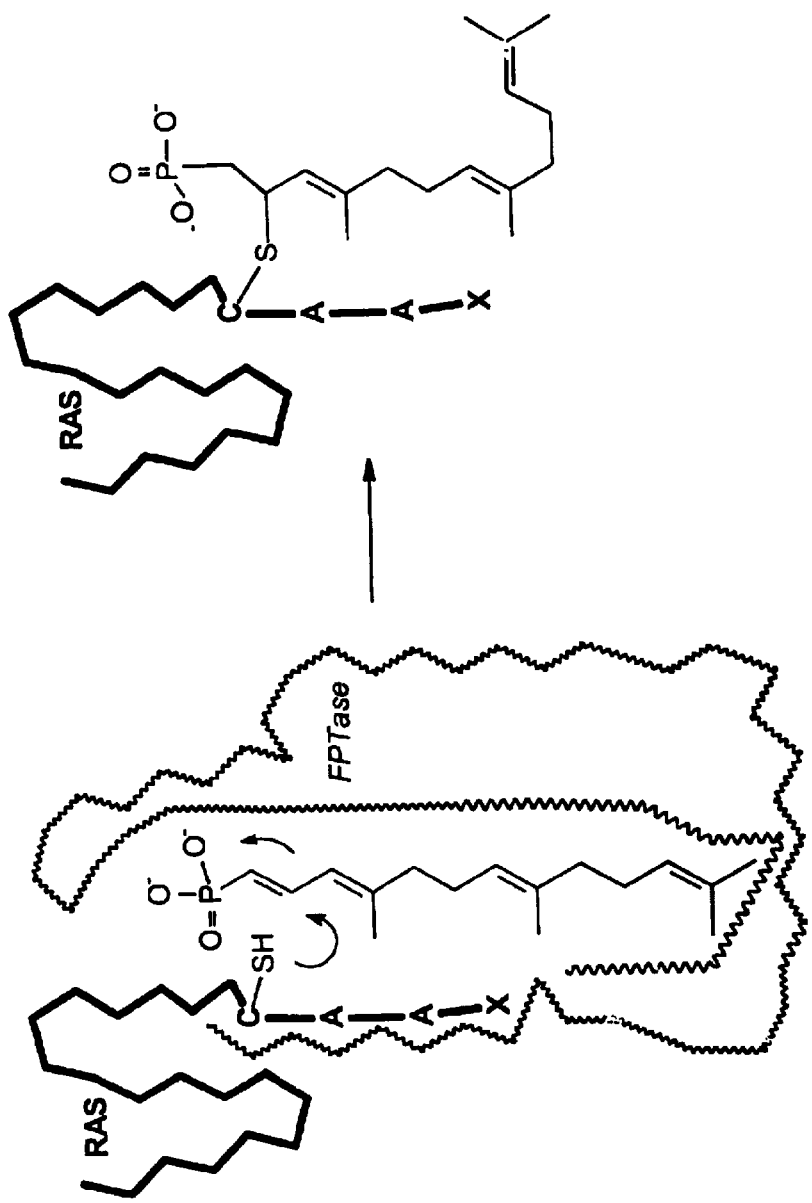
FIG. 3 schematically illustrates an FTPase mediated reaction of Ras with a vinyl phosphonate in embodiments of the present invention.

FIG. 3 shows schematically an example of a reaction with certain other analog compounds which afford an unnaturally modified Ras protein and which analog compound products or adducts may be unable to undergo retro-conjugate addition and therefore have greater stability and utility for inhibiting transferase enzymes and for probing the mechanism of various transferase enzymes and processes.

Other features of the invention will become apparent in the course of the following descriptions of exemplary embodiments which are given for illustration of the invention and are not intended to be limiting thereof.

Description of the Preferred Embodiments

EXAMPLE 1

Preparation of Fluorescent Analog Compounds

As exemplified in the reaction scheme below, Fischer esterification of commercial anthranilic acid provides the corresponding amino ester 54. Reductive amination of amine 54 with aldehyde 55, derived from $SeO_2$ oxidation of geranyl acetate and subsequent $MnO_2$ oxidation, gave the desired amine 56 and subsequent cleavage of the acetate gave the farnesol analog 57. The resulting farnesol analog (57) has a much greater degree of metabolic stability compared to other previously prepared analogs since this compound employs an amine linkage to bind an anthranilic acid to the terpenoid chain.

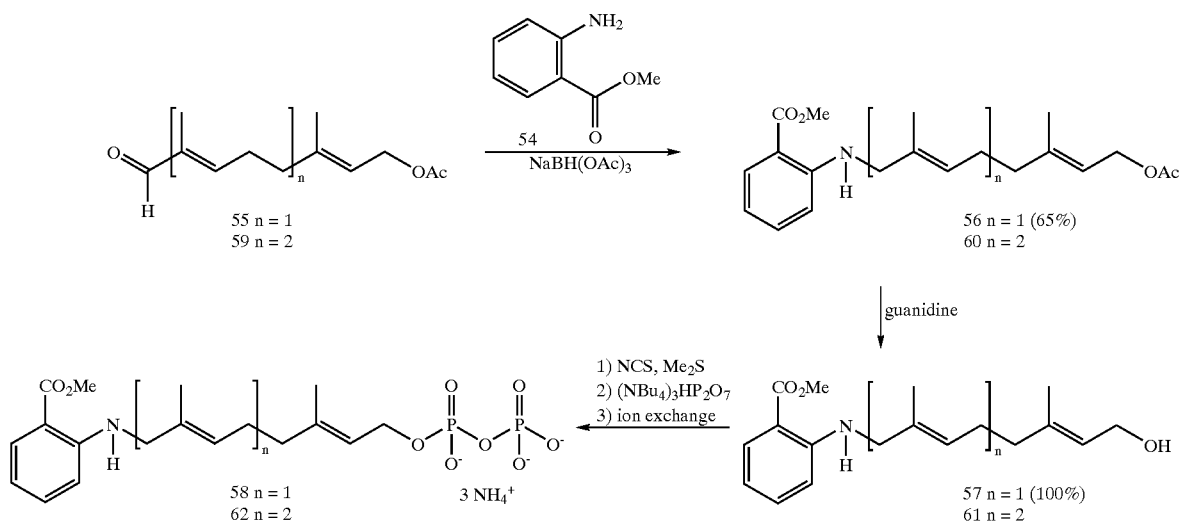

Compound 57 is highly fluorescent and it readily penetrates cell membranes to afford fluorescent cells. Compound 58 can be used in enzyme experiments with FPTase and Ras in order to obtain standard Ras proteins labeled with the fluorescent isoprenoid analog. Similarly compound 62 can be used with GGPTase I or II and proteins such as Rho B to obtain other protein standards. Protein standards obtained from in vitro experiments can then be used to analyze cell lysates for the formation of analogous proteins through in vivo experiments. Compound 58 $^1$H NMR($D_2O$) δ7.6 (1H), 7.2 (1H), 6.4 (2H), 5.4 (1H), 5.2 (1H), 4.4 (2H), 3.6 (3H), 3.4 (2H), 2.0 (2H), 1.8 (2H), 1.6 (3H), 1.4 (3H); and $^{31}$P NMR −6.9 (d, 1P) −9.75 (d, 1P).

EXAMPLE 2
Preparation of Fluorescent Analog Compounds

A second family of isoprenoid analogs can be prepared as shown below and have useful fluorescent properties based on aminonaphthalenesulfonic acids related to the dansyl group. Commercial 5-aminonaphthalene sulfonic acid (63) is first protected as its Boc derivative 64, and then converted to the N,N-dimethylsulfonamide (66) via the corresponding sulfonyl chloride (65). After cleavage of the Boc group, reductive amination is conducted with amine 67 and the aldehyde (68), derived from oxidation of prenyl acetate, affords the farnesol analog 69. The corresponding alcohol (70) can be used directly in whole cell experiments, and converted to the corresponding pyrophosphate (71) for either in vitro or in vivo use. The geranylgeraniol analog 73, as well as its pyrophosphate 74, can be obtained through parallel reactions if the geranyl acetate derivative 55 is used in the reductive amination, for example, to afford amine 72. Compound (73) $^1$H NMR(CDCl$_3$) δ8.20 (dd, 1H, J=6.23, 1.16 Hz), 8.12 (d, 1H, J=7.68 Hz), 8.09 (d, 1H, J=7.85 Hz), 7.49 (dd, 1H, J=7.30, 0.93 Hz), 7.46 (dd, 1H, J=8.80, 1.53 Hz), 6.68 (d, 1H, J=7.71 Hz), 5.48 (dt, 1H, J=5.81, 1.1 Hz), 5.38 (dt, 1H, J=68, 1.11 Hz), 4.15 (d, 1H, J=7.05 Hz), 4.10 (d, 1H, J=7.55 Hz), 3.82 (s, 2H), 2.82 (s, 6H), 2.24 (dd, 2H, J=14.48, 7.11 Hz), 2.09 (t, 2H, 7.78 Hz), 1.76 (s, 3H), 1.68 (s, 3H); $^{13}$C NMR(CDCl$_3$) δ144.1, 139.1, 133.1, 131.8, 130.3, 130.1, 128.9, 126.3, 126.0, 124.4, 123.8, 122.5, 114.1, 105.8, 59.3, 51.9, 39.1, 37.4(2C), 26.0, 16.2, 14.9; and High Resolution Mass Spectra m/z obsd. 403.2059 (M+H)$^+$, calcd for C$_{22}$H$_{31}$N$_2$O$_3$S 403.2055.

Advantages of naphthalene-based analogs include the dansyl-like compounds which can provide prenylated proteins with fluorescent properties that differ from those of the anthranilate-based compounds. One of ordinary skill in the art would expect an absorption maximum at about 340 nm but an emission maximum of about 540 nm for dansyl derivatives. In addition, if the dansyl-based compounds can serve as substrates, it might be possible to construct farnesol analogs with one set of spectral properties (e.g., based on anthranilate derivatives) and geranylgeraniol derivatives with a second set of properties (e.g., based on the larger dansyl group). The availability of fluorescent derivatives of both isoprenoid series as metabolic probes enables one to establish the ratio of farnesylation to geranylgeranylation under different conditions.

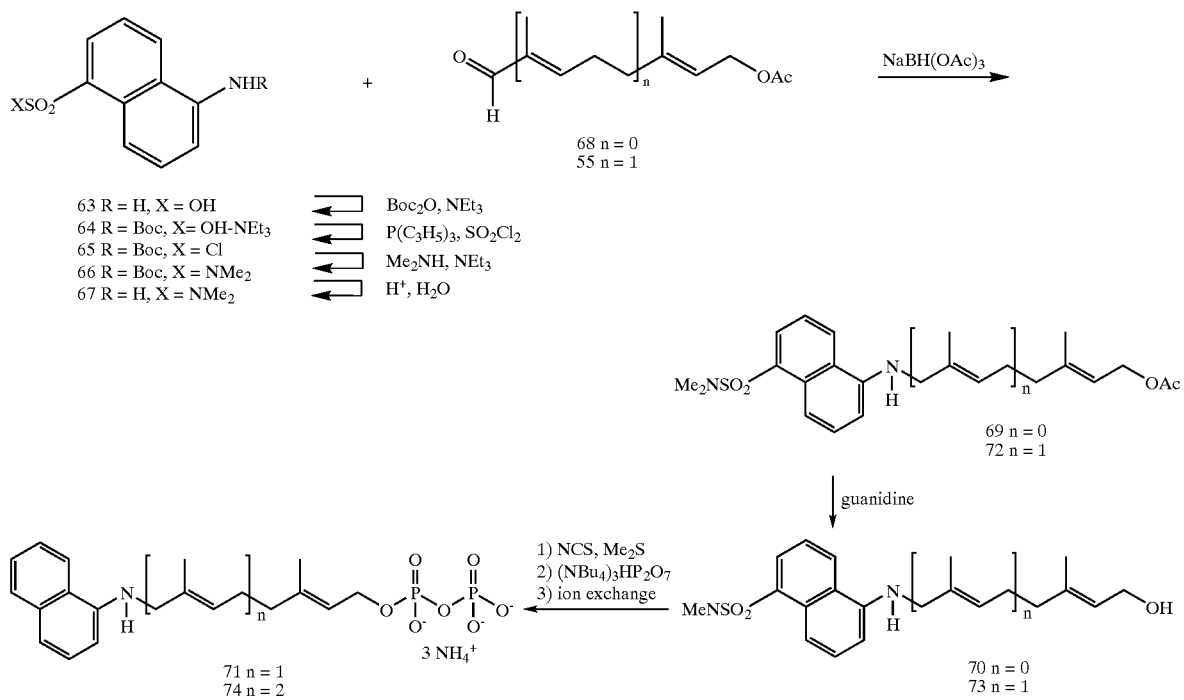

EXAMPLE 3

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |

-continued

|  |  |
|---|---|
| Sodium starch glycolate | 15.0 |
| Magnesium stearate | 5.0 |
|  | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |
| (iv) Injection 1 (1 mg/ml) | mg/ml |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art. Although specific quantities of "Compound X" are shown in the above illustrative examples, it is to be understood that the compounds can be present in any ratio provided the final formulation possesses the desired formulation properties.

All publications, patents, and patent documents are incorporated by reference herein in their entirety. The invention has been described with reference to various specific and preferred embodiments and techniques. However, it should be understood that many variations and modifications may be made while remaining within the spirit and scope of the invention.

References

Inhibition of Farnesyltransferase with A-176120, a Novel and Potent Farnesyl Pyrophosphate Analogue. Tahir, S. K.; Gu, W. Z.; Zhang, H. C.; Leal, J.; Lee, J. Y.; Kover, P.; Saeed, B.; Cherian, S. P.; Devine, E.; Cohen, J.; Warner, R.; Wang, Y. C.; Stout, D.; Arendsen, D. L.; Rosenberg, S.; Ng, S. C. Eur. J. Cancer, 2000, 36, 1161–1170.

Farnesyl Diphosphate-Based Inhibitors of RAS Farnesyl-Protein Transferase. Patel, D. V.; Schmidt, R. J.; Biller, S. A.; Gordon, E. M.; Robinson, S. S.; Manne, V. J. Med. Chem. 1995, 38, 2906–2921.

Cocrystal Structure of Protein Farnesyltransferase Complexed With A Farnesyl Diphosphate Substrate. Long, S. B.; Casey, P. J.; Beese, L. S. Biochemistry, 1998, 37, 9612–9618.

On the Stereochemical Course of Human Protein-Farnesyl Transferase. Mu, Y. -Q.; Omer, C. A.; Gibbs, R. A. J. Am. Chem. Soc. 1996, 118, 1817-1823.

Synthesis And Conformational Analysis of DI-C-13-Labeled Farnesyl Diphosphate Analogs. Zahn, T. J.; Ksebati, M. B.; Gibbs, R. A. Tetrahedron Lett. 1998, 39, 3991–3994. Evaluation of isoprenoid conformation in solution and in the active site of protein-farnesyl transferase using carbon-13 labeling in conjunction with solution- and solid-state NMR. Zahn T. J.; Eilers, M.; Guo, Z. M.; Ksebati, M. B.; Simon, M.; Scholten, J. D.; Smith, S. O.; Gibbs, R. A. J. Am. Chem. Soc. 2000, 122, 7153–7164.

Preparation of (2E,6E)-10,11-Dihydrofarnesol Via A (Bisphenyl)Dithioacetal Reduction. Mechelke, M. F.; Wiemer, D. F. Tetrahedron Lett. 1998, 39, 9609–9612.

Stereochemical Analysis of the Reaction Catalyzed By Yeast Protein Farnesyltransferase. Edelstein, R. L., Weller, V. A.; Distefano, M. D.; Tung, J. S. J. Org. Chem. 1998, 63, 5298–5299.

Synthesis of Farnesol Analogues Through Cu(I)-Mediated Displacements of Allylic THP Ethers By Grignard Reagents. Mechelke, M. F.; Wiemer, D. F. J. Org. Chem. 1999, 64, 4821–4829.

Novel Phosphonylphosphinyl (P—C—P—C—) Analogs of Biochemically Interesting Diphosphates—Synthesis And Properties of P—C—P—C— Analogs Of Isopentenyl Diphosphate And Dimethylallyl Diphosphate. McClard, R. W.; Fujita, T. S.; Stremler, K. E.; Poulter, C. D. J. Am. Chem. Soc. 1987, 109, 5544–5545.

Steady-State Kinetic Mechanism of RAS Farnesyl-Protein Transferase. Pompliano, D. L.; Rands, E.; Schaber, M. D.; Mosser, S. D.; Anthony, N. J.; Gibbs, J. B. Biochemistry 1992, 31, 3800–3807.

A PD(0)-Catalyzed Route To 13-Methylidenefarnesyl Diphosphate. Gibbs, R. A.; Krishnan, U. Tetrahedron Lett. 1994, 35, 2509–2512.

Cuprate-Mediated Synthesis And Biological Evaluation of Cyclopropyl- and Tert-Butylfarnesyl Diphosphate Analogs. Mu, Y.; Gibbs, R. A.; Eubanks, L. M.; Poulter, C. D. J. Org. Chem. 1996, 61, 8010–8015.

Farnesyl-Derived Inhibitors of RAS Farnesyl Transferase. Kang, M. S.; Stemerick, D. M.; Zwolshen, J. H.; Harry, B. S.; Sunkara, P. S.; Harrison, B. L. Biochem. Biophys. Res. Comm. 1995, 217, 245-249. f) Synthesis of Pyrophosphonic Acid Analogs of Farnesyl Pyrophosphate. Valentijn, A. R. P. M.; van den Berg, O.; van der Marel, G. A.; Cohen, L. H.; van Boom, J. H. Tetrahedron, 1995, 51, 2099–2108.

Photoactive Analogs of Farnesyl Pyrophosphate Containing Benzoylbenzoate Esters: Synthesis and Application to Photoaffinity Labeling of Yeast Protein Farnesyltransferase. Gaon, I.; Turek, T. C.; Weller, V. A.; Edelstein, R. L.; Singh, S. K.; Distefano, M. D. J. Org. Chem. 1996, 61, 7738–7745.

Stereochemistry-Dependent Inhibition of RAS Farnesylation By Farnesyl Phosphonic Acids. Hohl, R. J.; Lewis, K. A.; Cermak, D. M.; Wiemer, D. F. Lipids, 1998, 33, 39–46.

Phosphonate and Bisphosphonate Analogs of Farnesyl Pyrophosphate As Potential Inhibitors of Farnesyl Protein Transferase. Holstein, S. A.; Cermak, D. M.; Wiemer, D. F.; Lewis, K.; Hohl, R. J. Bioorganic & Medicinal Chemistry 1998, 6, 687–694.

Synthesis of Nonracemic Dimethyl Alpha-(Hydroxyfarnesyl)Phosphonates Via Oxidation of Dimethyl Farnesylphosphonate With (Camphorsulfonyl)

Oxaziridines. Cermak, D. M.; Du, Y.; Wiemer, D. F. *J. Org. Chem.* 1999, 64, 388–393.

Novel farnesol and geranylgeraniol analogues: A potential new class of anticancer agents directed against protein prenylation. Gibbs, B. S.; Zahn, T. J.; Mu, Y. Q.; Sebolt-Leopold, J. S.; Gibbs, R. A. *J. Med. Chem.* 1999, 42, 3800–3808.

Design and synthesis of a transferable farnesyl pyrophosphate analogue to Ras by protein farnesyltransferase. Chehade, K. A. H.; Andres, D. A.; Morimoto, H.; Spielmann, H. P. *J. Org. Chem.* 2000, 65, 388–393.

Phase I and Pharmacokinetic Study of Farnesyl Protein Transferase Inhibitor R115777 in Advanced Cancer. Zujewski, J.; Horak, I. D.; Bol, C. J.; Woestenborghs, R.; Bowden, C.; End, D. W.; Piotrovsky, V. K.; Chiao, J.; Belly, R. T.; Todd, A.; Kopp, W. C.; Kohler, D. R.; Chow, C.; Noone, M.; Hakim, F. T.; Larkin, G.; Gress, R. E.; Nussenblatt, R. B.; Kremer, A. B.; Cowan, K. H. *J. Clin. Oncol.* 2000, 18, 927–941.

Clinical and Biological Activity of the Farnesyltransferase Inhibitor R115777 in Adults with Refractory and Relapsed Acute Leukemias: A Phase I Clinical-Laboratory Correlative Trial. Karp, J. E.; Lancet, J. E.; Kaufmann, S. H.; End, D. W.; Wright, J. J.; Bol, K.; Horak, I.; Tidwell, M. L.; Leisveld, J.; Kottke, T. J.; Ange, D.; Buddharaju, L.; Gojo, I.; Highsmith, W. E.; Belly, R. T.; Hohl, R. J.; Rybak, M. E.; Thibault, A.; and Rosenblatt, J. *Blood.* 2001, 97, 3361–3369.

A Phase I Trial of the Farnesyl Transferase Inhibitor SCH66336: Evidence for Biological and Clinical Activity. Adjei, A. A.; Erlichman, C.; Davis, J. N.; Cutler, D. L.; Sloan, J. A.; Marks, R. S.; Hanson, L. J.; Svingen, P. A.; Atherton, P.; Bishop, W. R.; Kirschmeier, P.; Kaufman, S. H. *Cancer Res.* 2000, 60, 1871–1877.

Discovery and structure-activity relationships of imidazole-containing tetrahydrobenzodiazepine inhibitors of farnesyltransferase. Ding, C. Z.; Batorsky, R.; Bhide, R.; Chao, H. G. J.; Cho, Y.; Chong, S.; Gullo-Brown, J.; Guo, P.; Kim, S. H.; Lee, F.; Leftheris, K.; Miller, A.; Mitt, T.; Patel, M.; Penhallow, B. A.; Ricca, C.; Rose, W. C.; Schmidt, R.; Slusarchyk, W. A.; Vite, G.; Yan, N.; Manne, V.; Hunt, J. T. *J. Med. Chem.* 1999, 42, 5241–5253.

Discovery of (R)-7-cyano-2,3,4,5-tetrahydro-1-(1H-imidazol-4-ylmethyl)-3-(phenylmethyl)-4-(2-thienylsulfonyl)-1H-1,4-benzodiazepine (BMS-214662), a farnesyltransferase inhibitor with potent preclinical antitumor activity. Hunt, J. T. et al. *J. Med. Chem.* 2000, 43, 3587–3595.

Discovery of a Series of Cyclohexylethylamine-Containing Protein Farnesyltransferase Inhibitors Exhibiting Potent Cellular Activity. Henry, K. J; Wasicak, J.; Tasker, A. S.; Cohen, J.; Ewing, P.; Mitten, M.; Larsen, J. J.; Klavin, D. M.; Swenson, R.; Ng, S. C.; Saeed, B.; Cherian, S.; Sham, H.; Rosenberg, S. *J. Med. Chem.* 1999, 42, 4844–4852.

A Peptidomimetic Inhibitor of Farnesyl:Protein Transferase Blocks the Anchorage-Dependent and -Independent Growth of Human Tumor Cell Lines. Sepp-Lorenzino, L.; Ma, Z.; Rands, E.; Kohl, N. E.; Gibbs, J. B., Oliff, A.; Rosen, N. *Cancer Research*, 1995, 55, 5302–5309.

Geranylgeranylated RhoB Mediates Suppression of Human Tumor Cell Growth By Farnesyltransferase Inhibitors. Du, W.; Prendergast, G. C. *Cancer Res.* 1999, 59, 5492–5496.

Both Farnesylated and Geranylgeranylated RhoB Inhibit Malignant Transformation and Suppress Human Tumor Growth in Nude Mice. Chen, Z.; Sun, J.; Pradines, A.; Favre, G.; Adnane, J.; Sebti, S. M. *J. Biol. Chem.* 2000, 275, 17974–17978.

RhoB Alteration is Necessary for Apoptotic and Antineoplastic Responses to Farnesyltransferase Inhibitors. Liu, A.; Du, W.; Liu, J. P.; Jessell, T. M.; Prendergast, G. C. *Mol. Cell. Biol.* 2000, 20, 6105–6113.

Farnesyl transferase inhibitors block the farnesylation of CENP-E and CENP—F and alter the association of CENP-E with the microtubules. Ashar, H. R.; James, L.; Gray, K.; Carr, D.; Black, S.; Armstrong, L.; Bishop, W. R.; Kirschmeier, P. *J. Biol. Chem.* 2000, 275, 30451–30457.

Farnesyl Transferase Inhibitors Cause Enhanced Mitotic Sensitivity to Taxol and Epothilones. Moasser, M. M.; Sepp-Lorenzino, L.; Kohl, N. E.; Oliff A.; Balog, A.; Su, D. S.; Danishefsky, S. J.; Rosen, N. *Proc. Natl. Acad. Sci. USA*, 1998, [20, 139-148]95, 1369–1374.

Antitumor Efficacy of a Novel Class of Nonthiol-containing Peptidomimetic Inhibitors of Farnesyltransferase and Geranylgeranyltrasferase I: Combination Therapy with the Cytotoxic Agents Cisplatin, Taxol, and Gemcitabine. Sun, J.; Blaskovich, M. A.; Knowles, D.; Qian, Y.; Ohkanada, J.; Bailey, R. D.; Hamilton, A. D.; Sebti, S. M. *Cancer Res.* 1999, 59, 4919–4926.

The Phosphoinositide 3-OH Kinase/AKT2 Pathway as a Critical Target for Farnesyltransferase-Induced Apoptosis. Jiang, K.; Coppola, D.; Crespo, N. C.; Nicosia, S. V.; Hamilton, A. D.; Sebti, S. M.; Cheng, J. Q. *Mol. Cell. Biol.* 2000, 20, 139–148.

Cdk Inhibitors, Roscovitine and Olomoucine, Synergize with Farnesyltrasferase Inhibitor (FTI) to Induce Efficient Apoptosis of Human Cancer Cell Lines. Edamatsu, H.; Gau, C. L.; Nemoto, T.; Guo, L.; Tamanoi, F. *Oncogene*, 2000, 19, 3059–3068.

Inhibition of Protein Geranylgeranylation Causes a Superinduction of Nitric-oxide Synthase-2 by Interleukin-1$\beta$ in Vascular Smooth Muscle Cells. Finder, J. D.; Litz, J. L.; Blaskovich, M. A.; McGuire, T. F.; Qian, Y.; Hamilton, A. D.; Davies, P.; Sebti, S. M. *J. Biol. Chem.* 1997, 272, 13484–13488.

Farnesyl Pyrophosphate Synthase is the Molecular Target of Nitrogen-Containing Bisphosphonates. VanBeek, E.; Pieterman, E.; Cohen, L.; Lowik, C.; Papapoulous, S. *Biochem. Biophys. Res. Commun.* 1999, 264, 108–111.

HMG CoA Reductase Inhibitor-Induced Myotoxicity: Pravastatin and Lovastatin Inhibit the Geranylgeranylation of Low-Molecular Weight Proteins in Neonatal Rat Muscle Cell Culture. Flint, O. P.; Masters, B. A.; Gregg, R. E.; Durham, S. K. *Toxicol. Appl. Pharmacol.* 1997, 145, 99–110.

Nitrogen-Containing Bisphosphonates Inhibit the Mevalonate Pathway and Prevent Post-Translational Prenylation of GTP-Binding Proteins, Inducing Ras. Luckman, S. P.; Hughes, D. E.; Coxon, F. P.; Russell, R. G. G.; Rogers, M. J. *J. Bone Miner. Res.* 1998, 13, 581–589.

Preparation of diterpenoid derivatives as inhibitors of prenyl-protein transferase. Anthony, N. J.; Gomez, R. P.; Omer, U.S. Pat. No. 5,574,025, 1996. (CA 125: 86936.)

Intramolecular Fluorescence Enhancement: A Continuous Assay of RAS Farnesyl: Protein Transferase. Pompliano, D. L.; Gomez, R. P.; Anthony, N. J. *J. Am. Chem. Soc.* 1992, 114, 7945–7946.

2-(Acyloxy)ethylphosphonate Analogues of Prenyl Pyrophosphates: Synthesis and Biological Characterization. Cermak, D. M.; Wiemer, D. F.; Lewis, K.; Hohl, R. J. *Bioorg. Med. Chem.* 2000, 8, 2729–2737.

Lewis, K., Du, Y., Yang, L., Wiemer, D. F. Hohl, R. J. Effect of Combinations of Lovastatin and Specific Protein Isoprenylation Inhibitors on RAS and Mitogen Activated Protein (MAP) Kinase Activities. In Preparation.

Chemo-enzymatic synthesis of fluorescent Rab 7 proteins: Tools to study vesicular trafficking in cells. Owen DJ, Goody RS, et al., *Angew. Chem., Int. Ed. Eng.* 1999, 38, 509–512.

Phosphorylation of Isoprenoid Alcohols. Jo Davisson, V.; Woodside, A. B.; Neal, T. R.; Stremler, K. E.; Muehlbacher, M.; Poulter, C. D. *J. Org. Chem.* 1986, 51, 4768–4779.

Synthesis and DNA-Binding Properties of a Cisplatin Analog Containing a Tethered Dansyl Goup. Hartwig, J. F.; Pil, P. M.; Lippard, S. J. *J. Am. Chem. Soc.* 1992, 114, 8292–8293, and references cited therein.

The Dansyl Group as a Molecular Probe for the Histochemical Localization of a Synthetic Fibronectin-Related Peptide. Yamamoto, Y.; Katow, H.; Sofuku, S. *Chemistry Letters* 1994, 8, 1379–1382.

Enzymatic modification of proteins with a geranylgeranyl isorenoid. Casey P. J.; Thissen, J. A.; Moomaw, J. F. *Proc. Natl. Acad. Sci. U.S.A.* 1991, 88, 8631–8635.

The dually acylated NH2-terminal domain of gi 1 alpha is sufficient to target a green flourescent protein reporter to the caveolin-enriched plasma membrane domians. Palmitoylation of caveolin-1 is required for the recognition to dually acylated g-protein alpha subunits in vivo. Galbiati, F.; Volonte, D.; Meani, D.; Milligan, G.; Lublin, D. M.; Lisanti, M. P.; Parenti, M. *J. Biol. Chem.* 1999, 274, 5843–5850.

Regulation of insulin stimulated GLUT4 translocation by Munc 18c in 3T3L1 adipocytes. Thurmond, D. C.; Ceresa, B. P.; Okada, S.; Elmendorf, J. S.; Coker, K.; Pessin, J. E. *J. Biol. Chem.* 1998, 273, 33876–33883.

Inhibition of hydroxymethylglutaryl coenzyme A reductase activity induces a paradoxical increase in DNA synthesis in myeloid leukemia cells. Hohl, R. J.; Larson, R. A.; Mannickarottu, V.; Yachnin, S. *Blood* 1991, 77, 1064–1070.

Stereoelectronic Effects in Biomolecules. Gorenstein, D. G. *Chem. Rev.* 1987, 87, 1047–1077. b) Stereoelectronic Effects on the Conformation and Kinetics of Nucleophilic Displacement-Reactions in Epimeric 6-Membered Ring Phosphonate Diesters. Chang, J. W. A.; Gorenstein, D. G. *Tetrahedron*, 1987, 43, 5187–5196.

Targeted inactivation of the isoprenylcysteine carboxymethyltransferase gene causes mislocation of K-Ras in mammalian cells. Bergo, M. O.; Leung, G. K.; Ambroziack, P.; Otto, J. C.; Casey, P. J.; Young, S. G. *J. Biol. Chem.* 2000, 275, 17605–17610.

Mutational and Biochemical Analysis of Plasma Membrane Targeting Mediated by the Farnesylated, Polybasic Carboxy Terminus of K-ras4B. Roy, M. O.; Leventis, R.; Silvius, J. R. *Biochemistry* 2000, 39, 8298–8307.

What is claimed is:

1. A compound of formula I:

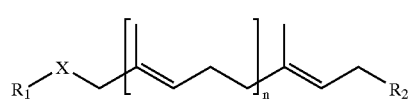

wherein:

X is —$NR_a$—;

$R_1$ is aryl selected from the group consisting of phenyl, naphthyl and anthracenyl, which aryl is optionally substituted with one or more substituents independently selected from —$COOR_b$, —$S(O)_nNR_bR_b$, halo, cyano, nitro, aryl, ($C_2$–$C_6$)alkenyl, —$C(=O)NR_bR_b$, —$OC(=O)NR_bR_b$, —$NR_bR_b$, or —$S(O)_nR_b$, where each $R_b$ is independently hydrogen, ($C_1$–$C_{10}$)alkyl, or ($C_1$–$C_{10}$)alkanoyl;

$R_2$ is
—O—P(=O)(—$OR_a$)$_2$,
—O—P(=O)(—$OR_a$)—O—P(=O)(—$OR_a$)$_2$,
—$CH_2$—O—P(=O)(—$OR_a$)$_2$,
—$CH_2$—O—P(=O)(—$OR_a$)—O—P(=O)(—$OR_a$)$_2$,
—$CH_2$—P(=O)(—$OR_a$)$_2$,
—CH{—P(=O)(—$OR_a$)$_2$}$_2$, or
—$CH_2$—P(=O)(—$OR_a$)—O—P(=O)(—$OR_a$)$_2$ each $R_a$ is independently hydrogen, ($C_1$–$C_{10}$)alkyl, ($C_1$–$C_{10}$)alkanoyl, ($C_1$–$C_{10}$)alkanoyloxy, ($C_1$–$C_{10}$)alkoxycarbonyl, or —$CH_2$—O—($C_1$–$C_{10}$)alkanoyl; n is independently 1, 2, or 3; or a pharmaceutically acceptable salt thereof.

2. The compound of claim 1 wherein $R_1$ is substituted phenyl.

3. The compound of claim 1 wherein $R_1$ is phenyl substituted with —$COOR_b$.

4. The compound of claim 1 wherein $R_1$ is 2-methoxycarboxy phenyl.

5. The compound of claim 1 wherein $R_1$ is substituted naphthyl.

6. The compound of claim 1 wherein $R_1$ is naphthyl substituted with a —$S(O)_nNR_bR_b$.

7. The compound of claim 1 wherein $R_1$ is naphthyl substituted at the 5-position with a —$S(O)_nNR_bR_b$ substituent.

8. The compound of claim 1 wherein $R_1$ is 5-N,N'-dimethylaminosulfonyl naphthy-1-yl.

9. The compound of claim 1 wherein $R_2$ is —O—P(=O)(—$OR_a$)$_2$.

10. The compound of claim 1 wherein $R_2$ is —O—P(=O)(—$OR_a$)—O—P(=O)(—$OR_a$)$_2$.

11. The compound of claim 1 wherein $R_2$ is —$CH_2$—O—P(=O)(—$OR_a$)$_2$.

12. The compound of claim 1 wherein $R_2$ is —$CH_2$—O—P(=O)(—$OR_a$)—O—P(=O)(—$OR_a$)$_2$.

13. The compound of claim 1 wherein $R_2$ is —$CH_2$—P(=O)(—$OR_a$)$_2$.

14. The compound of claim 1 wherein $R_2$ is —CH{—P(=O)(—$OR_a$)$_2$}$_2$.

15. The compound of claim 1 wherein $R_2$ is —$CH_2$—P(=O)(—$OR_a$)—O—P(=O)(—$OR_a$)$_2$.

16. The compound of claim 1 wherein $R_a$ is hydrogen.

17. The compound of claim 1 wherein $R_a$ is —C(=O)—$CH_3$.

18. The compound of claim 1 wherein $R_a$ is —$CH_3$.

19. The compound of claim 1 wherein $R_a$ is —$CH_2$—O—($C_1$–$C_6$)alkanoyl.

20. The compound of claim 1 wherein $R_b$ is hydrogen.

21. The compound of claim 1 wherein $R_b$ is —$CH_3$.

22. The compound of claim 1 wherein n is 1.

23. The compound of claim 1 wherein n is 2.

24. The compound of claim 1 wherein n is 3.

25. The compound of claim 1 wherein X is —NH—.

26. The compound of claim 1 wherein X is —N($CH_3$)—.

27. A pharmaceutical composition comprising a compound as described in claim 1 and a pharmaceutically acceptable diluent or carrier.

28. A method of inhibiting a prenylation transferase enzyme or synthase enzyme comprising contacting the enzyme with an effective amount of a compound as described in claim 1.

* * * * *

UNITED STATES PATENT AND TRADEMARK OFFICE
CERTIFICATE OF CORRECTION

PATENT NO. : 6,727,234 B2
DATED : April 27, 2004
INVENTOR(S) : Wiemer et al.

It is certified that error appears in the above-identified patent and that said Letters Patent is hereby corrected as shown below:

Column 1,
Line 56, delete "CAAX [(SEQ ID NO:51][)" and insert -- (CAAX) --, therefor.

Column 7,
Line 2, after "for" insert -- $R_2$ --.

Column 13,
Chemical Formula, below "$Boc_2O, NEt_3$" delete "$P(_{C3}H_5)_3, SO_2Cl_2$" and insert -- $P(C_6H_5)_3, SO_2Cl_2$ --, therefor.

Column 18,
Line 14, after "1998," delete "[20, 139-148]".

Signed and Sealed this

Twenty-third Day of November, 2004

JON W. DUDAS
*Director of the United States Patent and Trademark Office*